US011662403B2

(12) United States Patent
Piron et al.

(10) Patent No.: US 11,662,403 B2
(45) Date of Patent: May 30, 2023

(54) COIL ASSEMBLY FOR MAGNETIC RESONANCE IMAGING

(71) Applicant: SYNAPTIVE MEDICAL INC., Toronto (CA)

(72) Inventors: Cameron Anthony Piron, Toronto (CA); Alexander Gyles Panther, Toronto (CA); Sheryl Rae Thingvold, Toronto (CA); Chad Tyler Harris, Toronto (CA); Jeff Alan Stainsby, Toronto (CA)

(73) Assignee: Synaptive Medical Inc.

( * ) Notice: Subject to any disclaimer, the term of this patent is extended or adjusted under 35 U.S.C. 154(b) by 260 days.

(21) Appl. No.: 16/935,540

(22) Filed: Jul. 22, 2020

(65) Prior Publication Data

US 2020/0348381 A1 Nov. 5, 2020

Related U.S. Application Data

(63) Continuation of application No. 15/870,464, filed on Jan. 12, 2018, now Pat. No. 10,739,423, which is a continuation of application No. 14/910,400, filed as application No. PCT/IB2014/001864 on Sep. 17, 2014, now Pat. No. 9,897,668.

(60) Provisional application No. 61/897,050, filed on Oct. 29, 2013.

(51) Int. Cl.
| A61B 5/00 | (2006.01) |
| G01R 33/34 | (2006.01) |
| G01R 33/385 | (2006.01) |
| A61B 5/055 | (2006.01) |
| A61M 16/01 | (2006.01) |
| A61M 16/08 | (2006.01) |
| G01R 33/30 | (2006.01) |
| G01R 33/28 | (2006.01) |

(52) U.S. Cl.
CPC ...... *G01R 33/34053* (2013.01); *A61B 5/0042* (2013.01); *A61B 5/055* (2013.01); *A61M 16/01* (2013.01); *A61M 16/08* (2013.01); *G01R 33/30* (2013.01); *G01R 33/385* (2013.01); *G01R 33/3858* (2013.01); *G01R 33/283* (2013.01); *G01R 33/288* (2013.01); *G01R 33/34046* (2013.01)

(58) Field of Classification Search
CPC ...... A61B 5/0042; A61B 5/055; A61M 16/01; A61M 16/08; G01R 33/283; G01R 33/288; G01R 33/30; G01R 33/34046; G01R 33/34053; G01R 33/385; G01R 33/3858
See application file for complete search history.

*Primary Examiner* — Mark D Remaly

(57) ABSTRACT

A portable magnetic resonance imaging (MRI) system and methods, involving a magnet configured to generate a magnetic field, the magnet being a portable magnet transportable on a cart, and at least one coil assembly disposed in relation to the magnet, the at least one coil assembly having at least one gradient coil.

11 Claims, 20 Drawing Sheets

COIL ASSEMBLY FOR MAGNETIC RESONANCE IMAGING

CROSS-REFERENCE TO RELATED APPLICATIONS

This document is a continuation application, claiming the benefit of, and priority to: U.S. patent application Ser. No. 15/870,464, filed on Jan. 12, 2018, entitled "COIL ASSEMBLY FOR MAGNETIC RESONANCE IMAGING," U.S. patent application Ser. No. 14/910,400, filed on Feb. 5, 2016, entitled "COIL ASSEMBLY FOR MAGNETIC RESONANCE IMAGING," International Application No. PCT/IB2014/001864, filed on Sep. 17, 2014, entitled "COIL ASSEMBLY FOR MAGNETIC RESONANCE IMAGING," and U.S. Provisional Application Ser. No. 61/879,050, filed on Sep. 17, 2013, entitled "COIL ASSEMBLY FOR MAGNETIC RESONANCE IMAGING," all of which are hereby incorporated by reference in their entirety.

FIELD

The present disclosure relates to magnetic resonance imaging systems and methods.

BACKGROUND

In the related art, magnetic resonance imaging (MRI) is a medical imaging technique used in radiology to obtain images of an anatomy and the physiological processes thereof. MRI scanners use strong magnetic fields, magnetic field gradients, and radio waves to generate images of organs in a body.

SUMMARY

In accordance with an embodiment of the present disclosure, a magnetic resonance imaging system comprises: a magnet, e.g., a solenoid magnet and a portable magnet, configured to generate a magnetic field, e.g., a static magnetic field; and an annular coil assembly housed within at least a portion of the solenoid magnet, the coil assembly comprising a gradient coil, wherein the annular coil assembly has an aperture formed therein. Implementations may comprise one or more of the following features. The annular coil assembly and the magnet may be non-rotatable relative to each other such that a position of the aperture within the magnet is fixed. The annular coil assembly and the magnet may be rotatable relative to each other such that a position of the aperture within the magnet is variable. The magnetic resonance imaging system may further comprise a rotating mechanism configured to rotate the annular coil relative to the magnet; and a locking mechanism configured to lock the annular coil such that the coil is not rotatable relative to the magnet. A length of aperture may be shorter than a longitudinal length of the annular coil assembly. A length of the aperture may be about the same as the longitudinal length of the annular coil assembly. The magnetic resonance imaging system may further comprise a patient table slidable within the annular coil assembly.

In accordance with an embodiment of the present disclosure, the aperture may extend along a longitudinal direction of the annular coil assembly. The aperture may be located in the upper hemisphere of the annular coil assembly. The aperture may be located in the lower hemisphere of the annular coil assembly. The aperture may open one or more of the 'x', 'y', or 'z' axes of an annular coil assembly. For example, the aperture may be an opening in the 'x' and 'y' axes (and shields) while the 'z' axis (and shield) continues to form a complete cylinder. The aperture may be sized to house at least a portion of a breathing apparatus, an intraoperative device, an infusion apparatus, a display device, a projection screen, or a camera. The magnetic resonance imaging system may further comprise a display device, a projection screen, or a camera located within the aperture.

In accordance with an embodiment of the present disclosure, the annular coil assembly further comprise a transmit coil. The annular coil assembly may also comprise a receive coil. The magnetic resonance imaging system may further comprise a radio-frequency coil sized to encompass a subject's head, wherein the radio-frequency coil is configured to receive radio-frequency signals emitted from within the subject's head, and wherein coil assembly is sized to house the radio-frequency coil.

In accordance with an embodiment of the present disclosure, the gradient coil of the annular coil assembly is configured to provide a gradient variation to the static magnetic field in more than one spatial direction, and wherein none of the more than one spatial direction are directed at the aperture of the annular coil assembly. The main magnet may be a portable magnet transportable on a cart.

In accordance with an embodiment of the present disclosure, a method of providing a magnetic resonance imaging system, comprises: providing a solenoid magnet configured to generate a static magnetic field; and providing an annular coil assembly housed within at least a portion of the solenoid magnet, the coil assembly comprising a gradient coil, providing the annular coil assembly comprises forming an aperture therein that extends longitudinally along a central axis of the solenoid magnet to an edge of the solenoid magnet, and providing the annular coil assembly and the magnet comprises providing the annular coil assembly and the magnet as rotatable relative to each other, wherein a position of the aperture within the magnet is variable.

In accordance with an embodiment of the present disclosure, a method for imaging a subject comprises: placing a portion of the subject in an annular coil assembly housed within at least a portion of a solenoid magnet that is configured to generate a static magnetic field, wherein the annular coil assembly has an aperture formed therein; and initiating an imaging sequence to image the subject using the annular coil assembly and the solenoid magnet.

In accordance with an embodiment of the present disclosure, implementations comprise one or more of the following features. The method further comprises rotating the annular coil assembly relative to the solenoid magnet such that a portion of the subject is aligned with an apparatus, wherein at least a portion of the apparatus is housed within the aperture of the annular coil assembly. The method further comprises fixing the annular coil assembly relative to the magnet before initiating the imaging sequence.

In accordance with an embodiment of the present disclosure, the method further comprises loading the patient on a slidable table; and sliding the table into an inner bore of the solenoid magnet. The method further comprises passing a breathing tube through the aperture of the annular coil assembly to the subject's face that is aligned with the aperture; and providing anesthesia to the subject through the breathing tube while the subject is being imaged. The method further comprises inserting a radio-frequency (RF) receiver coil into the aperture of the annular coil assembly before initiating the imaging sequence.

In accordance with an embodiment of the present disclosure, the method may further include rotating the annular coil assembly relative to the magnet causes the radio-frequency receiver coil to be placed at an access port on the subject's head through which an interventional procedure is being performed; and initiating the imaging sequence further comprises using the radio-frequency receiver coil to image the subject during the interventional procedure based on the access port. The method may further comprise communicating with the subject while the subject is being imaged using a display device or projection screen housed within the aperture of the annular coil assembly. The method may further comprise monitoring the subject while the subject is being imaged using a camera device housed within the aperture of the annular coil assembly.

BRIEF DESCRIPTION OF DRAWINGS

Embodiments will now be described, by way of example only, with reference to the drawings, in which.

DETAILED DESCRIPTION

Figure 1A:
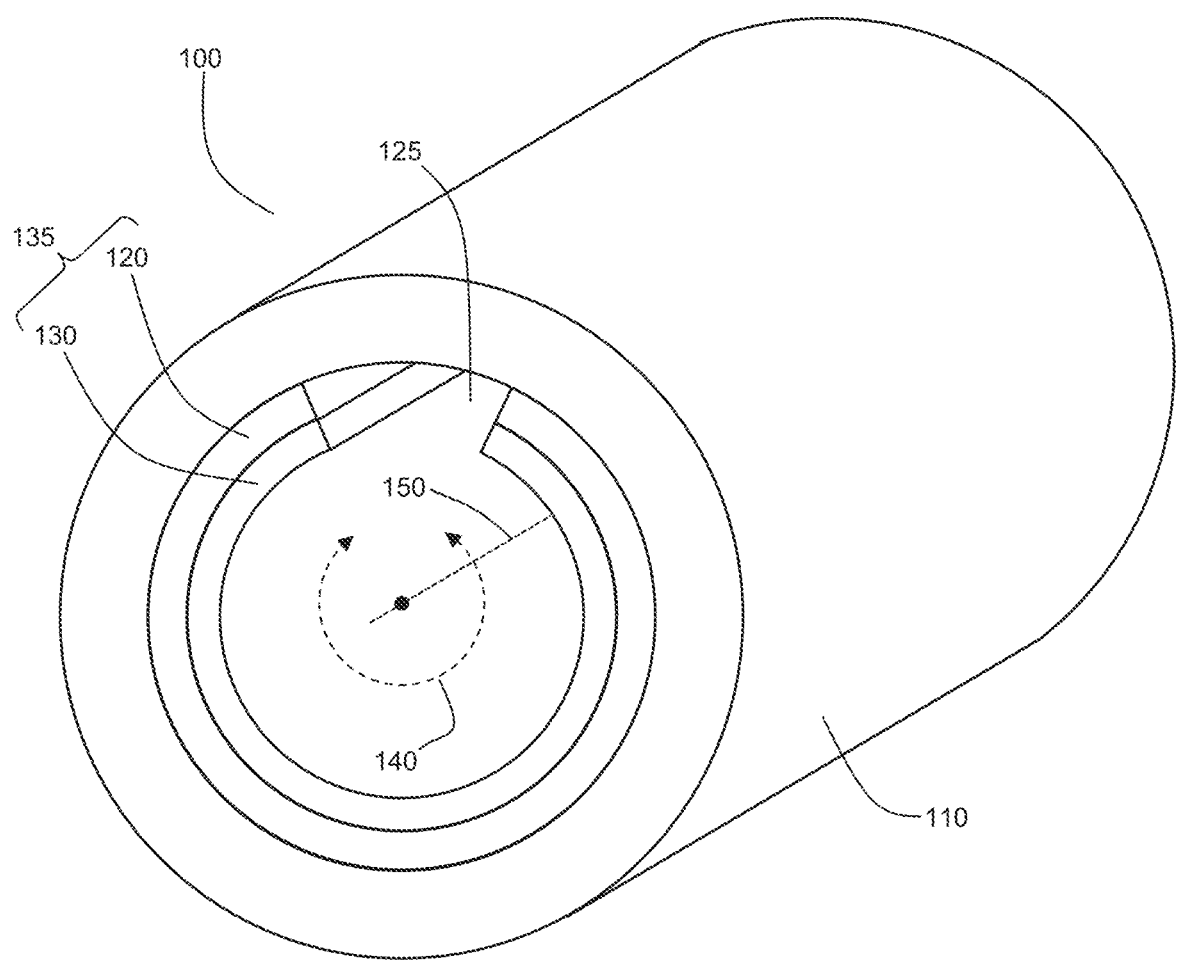
FIG. 1A is a diagram illustrating a magnetic resonance imaging system, wherein the transmit coil and gradient coil are rotatably provided within a magnet, such as a solenoid magnet, and wherein an aperture is provided within the transmit and gradient coils, in accordance with an embodiment of the present disclosure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

According to selected embodiments of the present disclosure, magnetic resonance imaging systems and devices are provided in which an aperture (e.g. a gap, opening, cavity or window) is formed within a coil assembly comprising the gradient and transmit coils (and optionally a receive coil). In some implementations, the coil assembly can be rotated relative to an axis within the bore of the main solenoid magnet. In some implementations, the coil assembly may not rotate and the aperture can be fixed.

As described in further detail below, the rotatable aperture may be employed to provide access and/or visibility to a patient who is being imaged. The aperture may be employed to create a window or portal for medical staff to view and monitor the patient. The aperture may also provide a spatial region for medical equipment or devices to be accommodate or housed during a magnetic resonance imaging scan. In some implementations, the aperture may be located in the upper half, for example, on top, of the inner surface of the coil assembly. These implementations may facilitate, for example, functional MR imaging of the brain, intra-operative imaging of neurological interventions. In some implementations, the aperture may be in the lower half, for example, at the bottom, of the inner surface of the coil assembly. These implementations may accommodate, for example, a mammography application, an MR-guided breast biopsy procedure, etc. As shown in several examples below, the aperture can be rotated within the solenoid magnet to accommodate various patient positions, and can be located as needed for desired accessibility. For example, typically, the gradients and RF transmit coils are built as cylinders around the same axis as the solenoid magnet used to generate the main field. By opening up an aperture in the gradient coils and RF transmit coil, it is possible to generate extra space inside the MRI without sacrificing performance. By then rotating these gradients and RF coils, it is possible to locate the area of extra space where it would be of most use during a surgical procedure, for example, to allow more room for an intubated patient with anesthesia equipment, or to allow an insert imaging device such as a port coil to be used. This rotating is possible because all of MRI relies on the use of orthogonal planes. As the main magnetic field (B0) remains constant in the 'z' direction, as long as the directions of the gradients and RF remain substantially orthogonal then performance may be maintained.

Referring to FIG. 1A, this diagram illustrates a magnetic resonance imaging system, wherein a coil assembly 135, comprising transmit coil 130 and gradient coil 120, is rotatably provided within solenoid magnet 110, in accordance with an embodiment of the present disclosure. Aperture 125 is provided within the coil assembly, forming an opening or a gap in the coil assembly 135. Coil assembly 135 may generally be shaped as an annular structure and housed within the inner bore of solenoid magnet 110. Under rotation of coil assembly 135 relative to central axis 150, as shown at 140, aperture 125 may be positioned at various angular locations within the inner bore of the solenoid magnet. The gradient, transmit, and receive coil system may rotate either automatically or manually. In some implementations, annular coil assembly 135 only comprises gradient coil 120. In these implementations, annular coil assembly does not include transmit coil 130 or any receiver coil. For these implementations, radio-frequency (RF) signals are, for example, transmitted by local coils for imaging a subject. In one instance, a head coil in a birdcage configuration is used for both transmitting and receiving RF signals for imaging the subject. In another instance, a surface coil is used for transmitting an RF signal into the subject and a phased array coil configuration is used for receiving MR signals in response. The embodiments provided herein may be adapted for intraoperative MRI, and MRI systems for use in an emergency room setting.

Figure 1B:
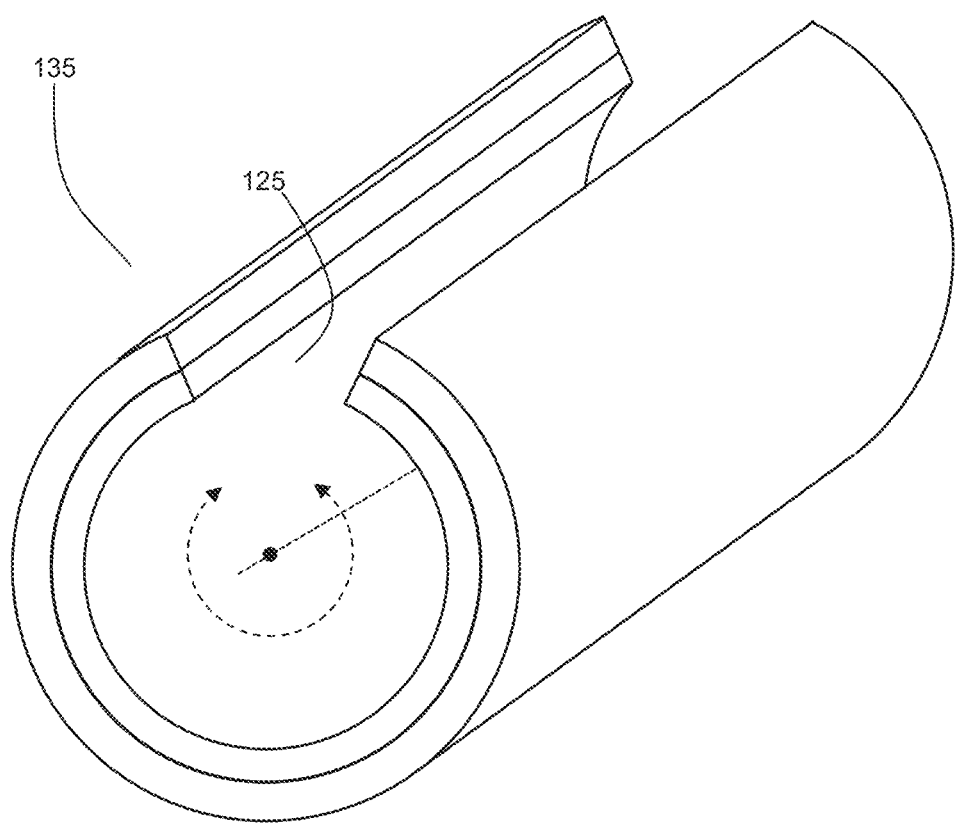
FIG. 1B is a diagram illustrating a rotatable coil assembly, comprising the transmit and gradient coils, in accordance with an embodiment of the present disclosure.

Referring to FIG. 1B, this diagram illustrates a detailed view of an implementation of the coil assembly 135, in which the aperture 125 is provided as an opening formed along the longitudinal direction of the coil assembly 135, in accordance with an embodiment of the present disclosure. In one instance, the aperture 125 may only extend over a portion of the full longitudinal extent of the coil assembly 135. In other instances, two or more apertures may be provided at various axial and/or azimuthal positions of the coil assembly 135. In fact, a variety of apertures with varying angular ranges may be formed on coil assembly 135.

Figure 2A:
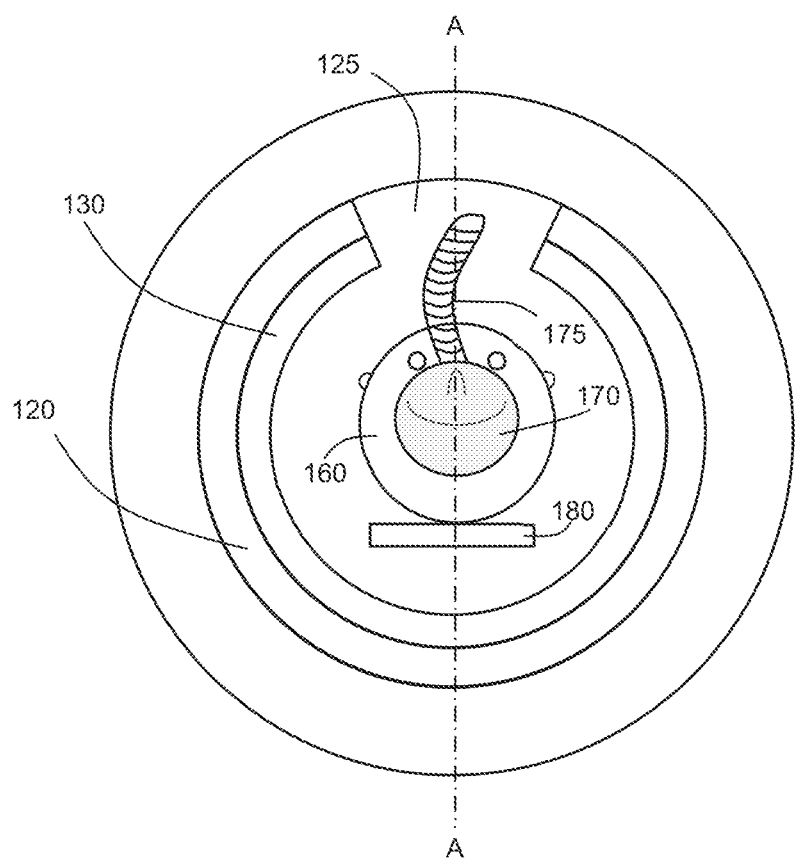
FIG. 2A is a diagram illustrating the use of the aperture within the rotatable transmit and gradient coil assembly for accommodating additional medical devices or equipment, in accordance with an embodiment of the present disclosure.

Referring to FIG. 2A, this diagram illustrates an implementation of the aperture within the rotatable transmit and gradient coil assembly for accommodating additional medical devices or equipment, in accordance with an embodiment of the present disclosure. This axial view illustrates an example of providing an anesthetic mask for an intubated patient. In this example, patient 160 is positioned on patient support 180. Patient support 180 comprises a slidable patient table. An anesthetic mask 170 and associated tubing 175 are provided on intubated patient 160. Aperture 125 is oriented to provide additional room to house tubing 175, without comprising valuable space within coil assembly 135 between transmit coil 130 and patient 160.

Figure 2B:
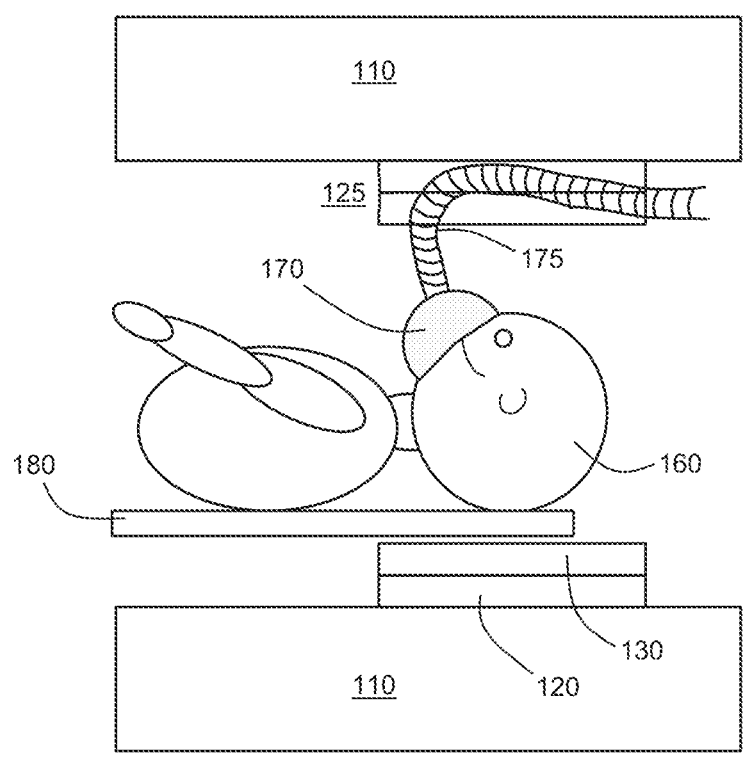
FIG. 2B is a diagram illustrating, in a longitudinal view, the use of the aperture within the rotatable transmit and gradient coil assembly for accommodating additional medical devices or equipment, shown as shown in FIG. 2A, along across-section, in accordance with an embodiment of the present disclosure.

Referring to FIG. 2B, this diagram illustrates a longitudinal view of the implementation of the aperture, shown as a cross-section taken along line A-A in FIG. 2A, in accordance with an embodiment of the present disclosure. This longitudinal view shows a manner in which a tubing 175 is received within the aperture that would have otherwise been occupied by gradient coil 120 and transmit coil 130. The tubing 175 takes up space towards the top of the inner bore of the solenoid magnet 110. This space overlaps with coil assembly 135 if coil assembly is a full annular coil assembly. The aperture 125 on coil assembly 135 provides the space for tubing 175 without compromising gradient coil 120 and transmit coil 130.

Figure 2C:
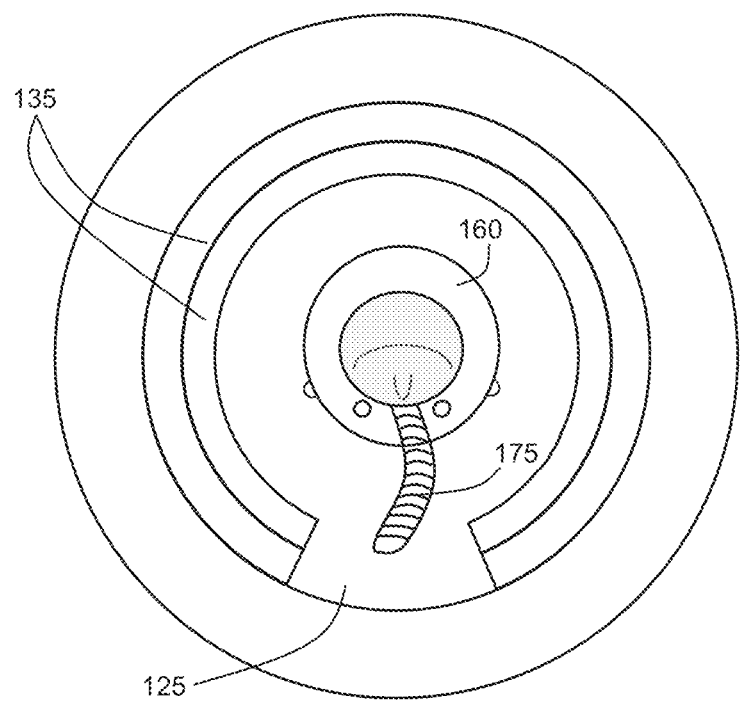
FIG. 2C is a diagram illustrating the rotation of the aperture to accommodate a patient oriented in a prone position, in accordance with an embodiment of the present disclosure.

Referring to FIG. 2C, this diagram illustrates a manner in which the rotatable aspect of coil assembly 135 is employed to accommodate a patient 160 oriented in a prone position, in accordance with an embodiment of the present disclosure. Since aperture 125 rotates with coil assembly 135, the additional medical hardware or devices, associated with the patient (in this case, the tubing 175), are accommodated in more than one angular position.

Figure 2D:
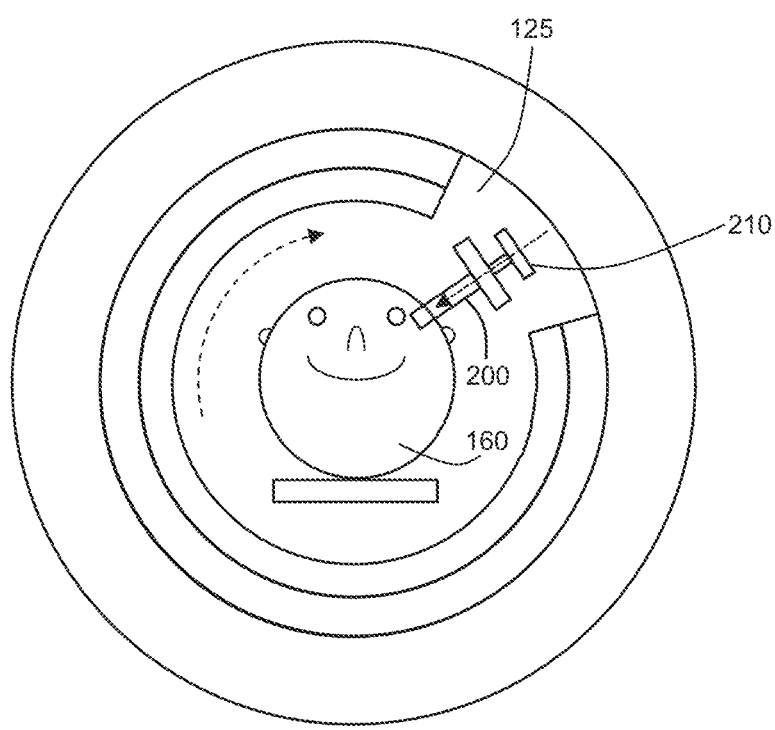
FIG. 2D is a diagram illustrating the rotation of the aperture to accommodate medical devices associated with a neurological interventional procedure, in accordance with an embodiment of the present disclosure.

Referring to FIG. 2D, this diagram illustrates rotating the aperture 125 to accommodate medical devices associated with a neurological interventional procedure, wherein a patient 160 has an access port 200 inserted within his head, in accordance with an embodiment of the present disclosure. The rotatable aperture 125 need not be positioned over the patients face, and the extra space afforded by aperture 125 may be employed to position a local MRI receiver 210, e.g., implemented as a RF receiver coil, at the relevant surgical or diagnostic location. This may prove advantageous during port-based neurological surgical and diagnostic procedures in allowing for magnetic resonance images to be obtained intra-operatively without having to remove the access port prior to imaging. For example, the close proximity of the local MM receiver 210 may provide superior signal-to-noise performance to improve sensitivity or to increase frame rate of an intraoperative MRI imaging procedure.

Figure 3A:
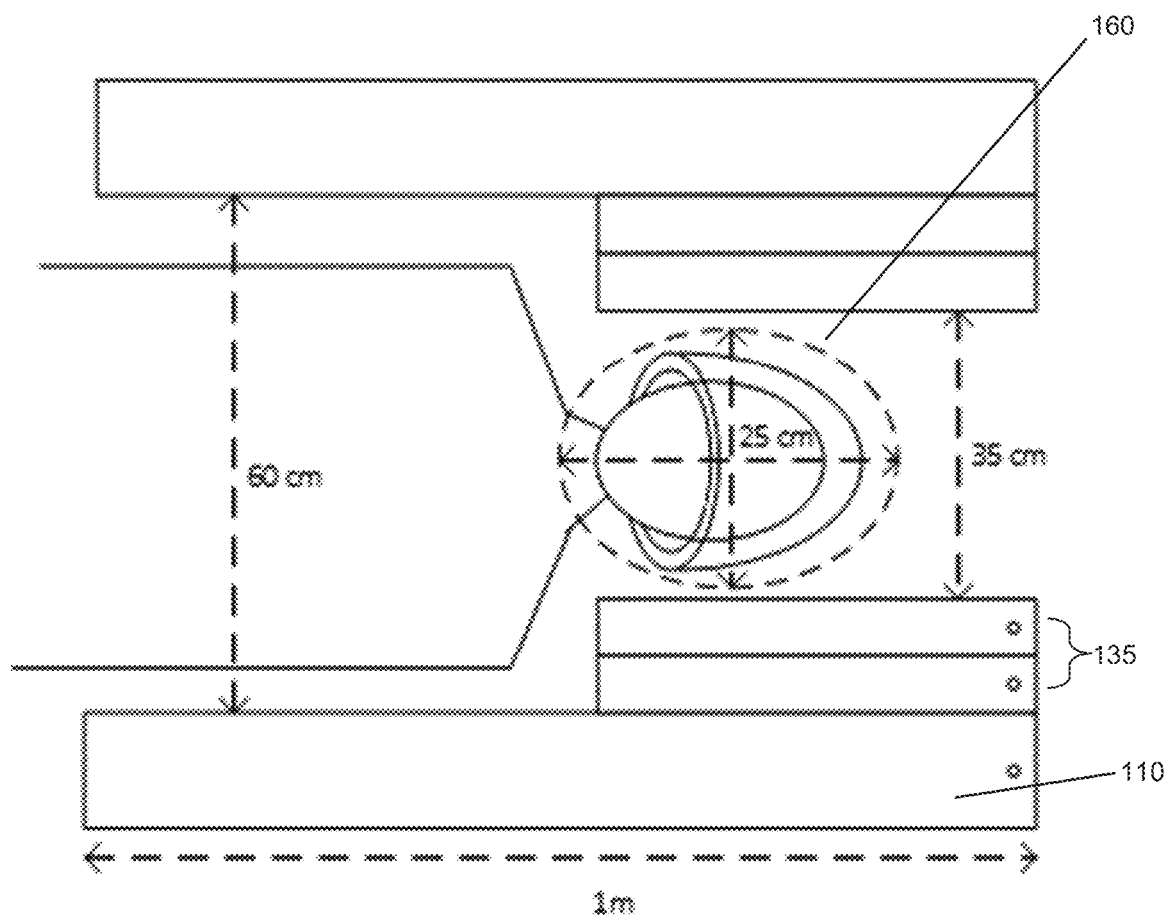
FIG. 3A is a diagram illustrating, in a top view, a patient disposed within an MRI scanner, the coil assembly being in close proximity relative to the patient head, in accordance with an embodiment of the present disclosure.

Referring to FIG. 3A, this diagram illustrates a top-down view of a patient positioned within a magnetic resonance imaging system in which the coil assembly 135 is recessed within solenoid magnet 110, in accordance with an embodiment of the present disclosure. This example shows the close proximity that can be achieved between the coil assembly and the patient's head 160, while still providing ample room for other portions of the patient's body that are not necessarily being imaged. The dimensions provided in this figure are example ranges and are not intended to be limiting.

Still referring to FIG. 3A, embodiments of the present disclosure may enable a reduction in size of a magnetic resonance imaging system, as the presence of the rotatable aperture may enable a patient to be accommodated in a bore with a smaller diameter. For example, as described elsewhere in the present disclosure, the rotatable aperture may be employed to accommodate one or more additional devices, such as diagnostic, therapeutic, imaging or communications devices, without requiring an associated increase in the bore diameter. In other embodiments, the rotatable aperture may be employed to provide the patient with the perception of additional room within the scanner by providing additional room in the vicinity of the patient's face (for example, within a small annular segment associated with the size of the patient's face), while still maintaining close proximity between the coil assembly elsewhere.

Still referring to FIG. 3A, this ability to perform magnetic resonance imaging within a smaller bore system can lead to advantages in performance and/or cost. A typical magnetic resonance imaging system may have a central bore (within the transmit coil) diameter of approximately 60 cm. A wide-bore system may have a diameter of approximately 70 cm. The cost of such a system is governed in part by the radius of the bore, because the radius affects the stored energy in the solenoid magnet. The stored energy varies as the cube of the radius. As such, reducing the size of the bore is advantageous as it allows for cost reduction and/or an increase of the achievable primary magnetic field.

Still referring to FIG. 3A, similarly, the performance of the gradient coil is also strongly dependent on the radius, because the magnetic field from a wire drops according to an inverse square law. Accordingly, a size reduction in the gradient coil radius allows one to achieve a given performance with less current, thereby reducing the system cost and complexity (and reducing associated heating and cooling requirements).

Still referring to FIG. 3A, accordingly, in some embodiments, the diameter of the transmit coil may be reduced from the typical values noted above. In some example implementations, the inner diameter of the transmit coil may be reduced to a value that accommodates the insertion of a head, but is, for example, less than approximately 60 cm, less than approximately 50 cm, less than approximately 45 cm, less than approximately 40 cm, and less than approximately 35 cm. As shown in FIGS. 2A and 2B, 3D and 5E, the coil assembly may be recessed within the solenoid magnet, such that the patient body (e.g. the shoulders) may be inserted within a broader diameter region (for example, having a diameter of approximately 60 cm) associated with the coil assembly, while inserting the head within a narrower diameter region associated with the coil assembly. For example, in one example implementation, shown in FIG. 5E, the solenoid magnet may have a longitudinal (axial) length of approximately 1 m, while the region associated with the coil assembly (the gradient and transmit coils) may have a longitudinal (axial) length of approximately 0.5 m.

Figure 3B:
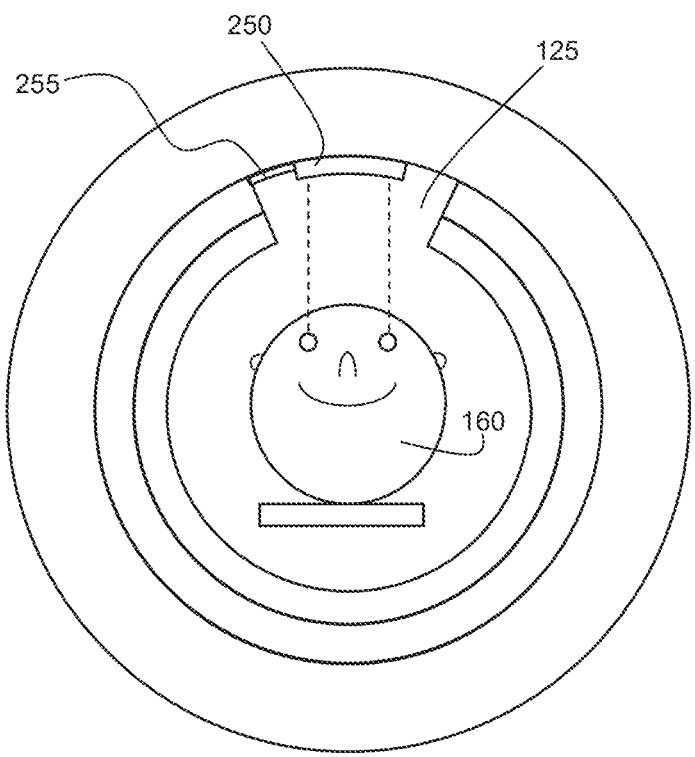
FIGS. 3B and 3C, together, are diagrams illustrating the aperture being employed to allow the patient to view an image or video, in accordance with some embodiments of the present disclosure.
Figure 3C:
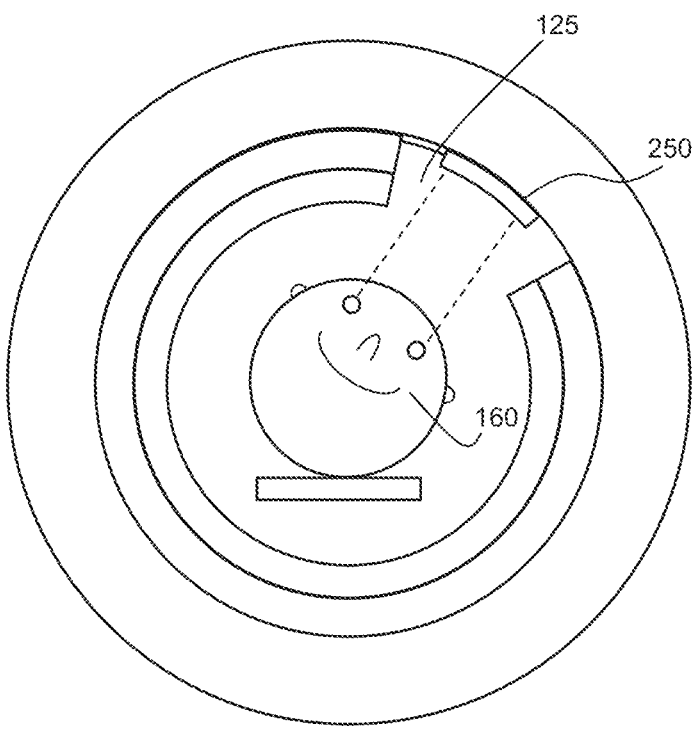

Referring to FIGS. 3B and 3C, together, these diagrams illustrate a manner in which the aperture is employed to allow patient 160 to view an image or video, for example, via an MRI-compatible display device or projection screen 250 located in aperture 125 within the inside of the solenoid magnet, in accordance with some embodiments of the present disclosure. The display or projection device 250 may be attached to the coil assembly, for example via member 255. FIGS. 3B and 3C show two different angular orientations, illustrating a manner in which the patient 160 may view and/or interact with the display or projection device 250 at multiple orientations.

Still referring to FIGS. 3B and 3C, according, in some embodiments, an MRI with a video screen or image projection may be embedded within the mechanism to facilitate communication with the patient. This screen can be used to provide scan information to the patient (such as instructions to not move, or to count down the scan time remaining) or provide visual cues during scanning, for example fMRI studies. Alternatively, this screen may be used to provide entertainment during the scanning procedure. If an MR-compatible camera is added, this screen or image projection may be used for two-way communications between a patient in the scanner and another individual. The screen or image projection and camera can also potentially be mounted to the rotating items such that the patient remains visible regardless of the aperture orientation.

Still referring to FIGS. 3B and 3C, in one example embodiment, a timer may be visible to the patient inside of the scanner. This timer would allow the patient to see an indication of time remaining or time elapsed for their current scan, and could better hold still, leading to fewer image artifacts. If a general screen or area for image projection was available to the patient, the timer could be displayed here, along with instructions to stay still, and soothing images, or other entertainment. The screen or image projection could be used for fMRI studies. If the screen or image projection were combined with a camera, two way visual contact could be achieved between the patient in the scanner and the operator. This contact could be used to allow medical staff to watch a medically distressed patient, or a child to be in visual contact with their caregiver. The medical staff could explain the time to the patient, leading to a less confusing and isolating experience.

Figure 3D:
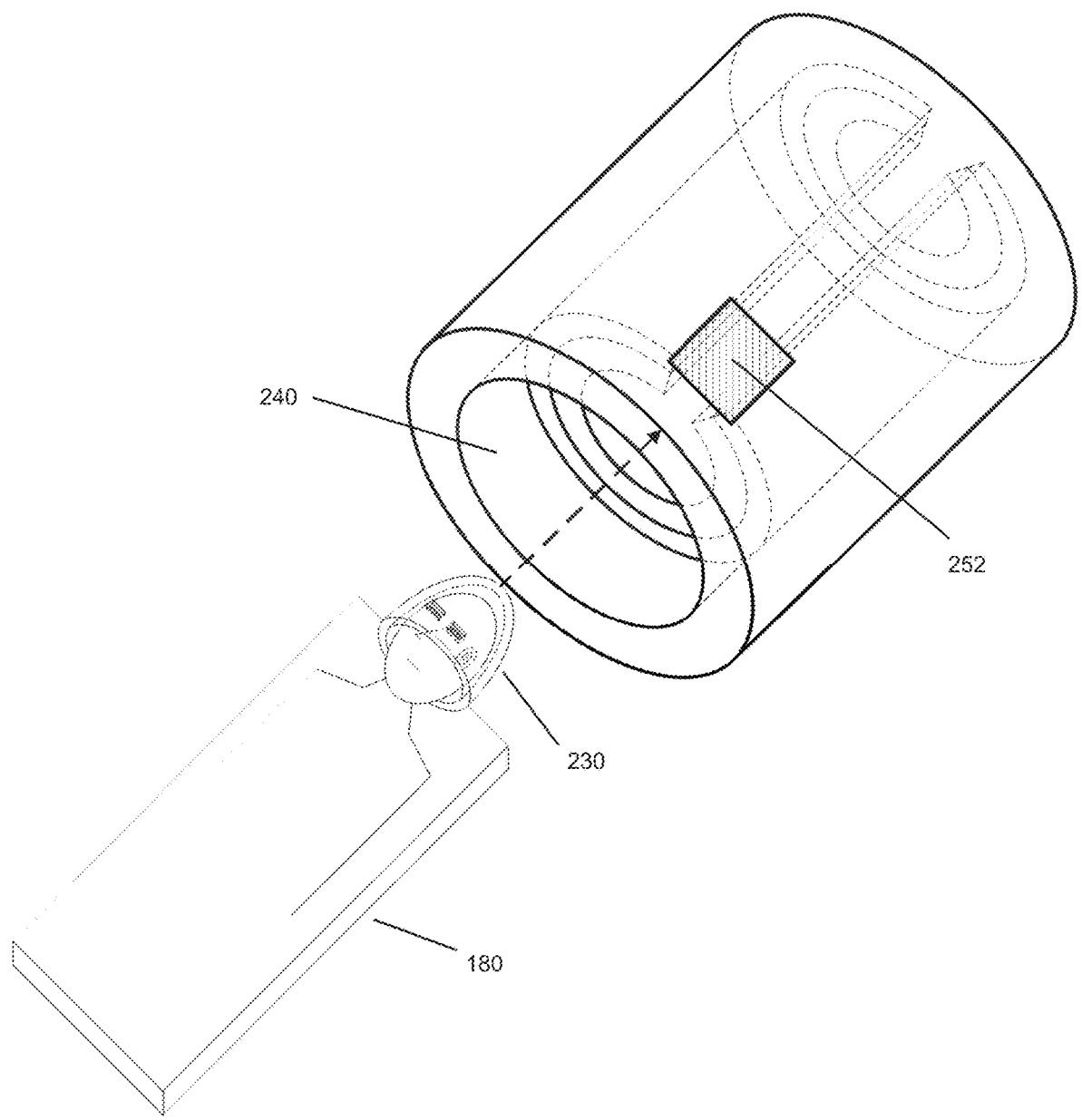
FIG. 3D is a diagram illustrating the insertion of patient, wearing a head coil, into a magnetic resonance imaging system, having a coil assembly with an aperture formed therein, in accordance with an embodiment of the present disclosure.

Referring to FIG. 3D, this diagram illustrates insertion of patient 160, supported by a table or stretcher 180, and wearing a head coil 230, into a magnetic resonance imaging system having a coil assembly with an aperture formed therein, in accordance with an embodiment of the present disclosure. In one instance, head coil 230 can be configured as a radio-frequency receiver coil as a local coil. In this instance, head coil 230 is configured to receive radio-frequency signals emitted from within the subject's head and in response to excitation radio frequency pulses sent from the transmit coil 130 within the annular coil assembly 135. In another instance, head coil 230 can be configured as a radio-frequency transmit and receiver coil. The aperture comprises a display device, screen and/or camera 252. The coil assembly and associated aperture may be rotatable to accommodate multiple patient orientations. The system comprises an initial gap region 240 configured to accommodate the patient's shoulders and torso. The receiving coil may be positioned about the patient with the aperture as desired prior to installing them within the magnet. In this embodiment, the rotating coil assembly 135 comprises the gradient coil 120 and transmitting coil 130.

Figure 3E:
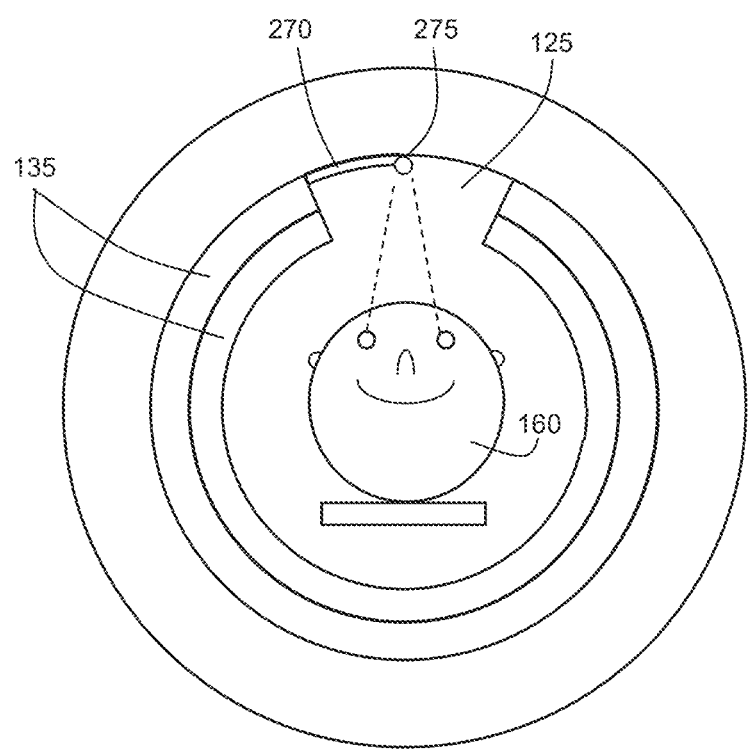
FIG. 3E is a diagram illustrating a camera disposed within the solenoid and coupled with the rotating coil assembly, wherein the patient is visually monitored while inside the MRI scanner at multiple orientations, in accordance with an embodiment of the present disclosure.

Referring to FIG. 3E, this diagram illustrates an MRI system, wherein a camera 275 is positioned inside aperture 125 and attached to rotating coil assembly 135 (for example, via attachment member 270), so that patient 160 can be visually monitored while inside the scanner at multiple orientations, in accordance with an embodiment of the present disclosure. Such an embodiment may be optionally combined with the embodiment, as shown in FIGS. 3B and 3C, to provide a display mechanism in addition to a camera, for example, to allow two-way visual communication or interaction between a patient in the scanner and another individual. By positioning an MR compatible camera, e.g., for eye-tracking in fMRI studies, on the rotating element, enabling the anesthetist to maintain visual contact with the patient regardless of their orientation.

Figure 4A:
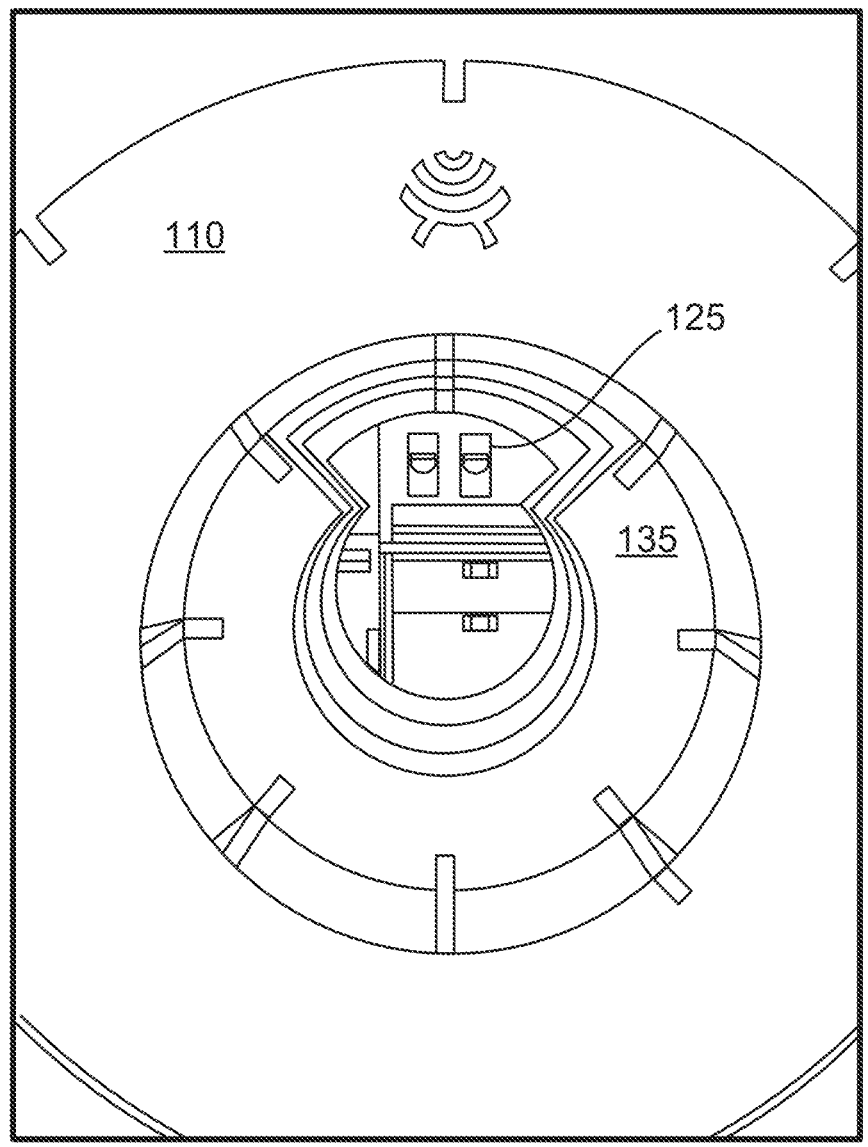
FIG. 4A is a photograph illustrating a wooden prototype of an example system, comprising a rotatable coil assembly recessed within a MRI magnet, in accordance with an embodiment of the present disclosure.
Figure 4B:
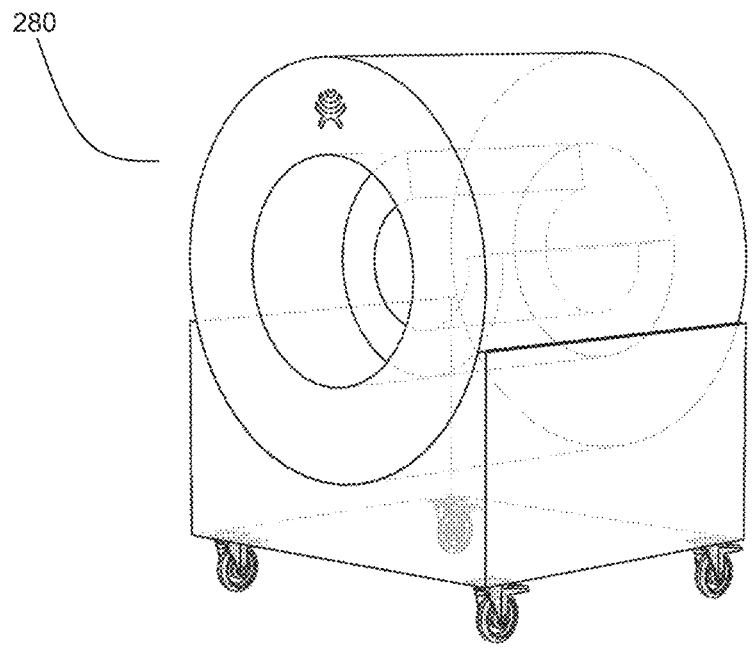
FIGS. 4B and 4C, together, are diagrams illustrating a portable magnetic resonance imaging system, wherein the rotatable coil assembly is recessed within the magnet bore, showing (a) a front view and (b) a rear view, in accordance with some embodiments of the present disclosure.
Figure 4C:
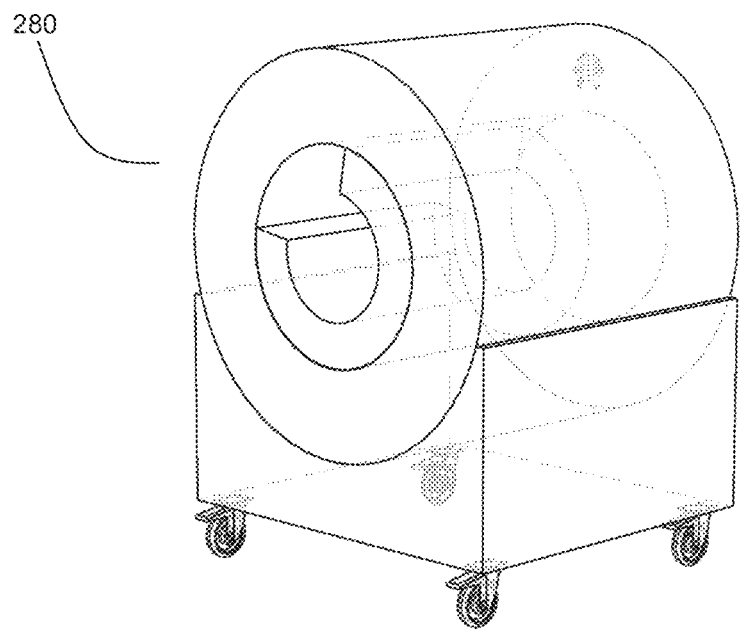

Referring to FIGS. 4A, 4B, and 4C, together, these photographs illustrate a wooden prototype of an example system comprising a rotatable coil assembly 135 recessed within an MRI magnet 110, in accordance with some embodiments of the present disclosure. FIG. 4A illustrates the rotatable coil assembly 135 having an aperture 125. FIGS. 4B and 4C illustrate examples of a portable magnetic resonance imaging system 280 according to an embodiment in which the rotatable coil assembly is recessed within the magnet bore, showing (a) a front view and (b) a rear view. In some instances, the magnet is portable in that it can travel within a room or between rooms, and may be mounted on wheels, with or without a motorized base. The magnet may have a tether cable attaching it to an equipment room.

Figure 5A:
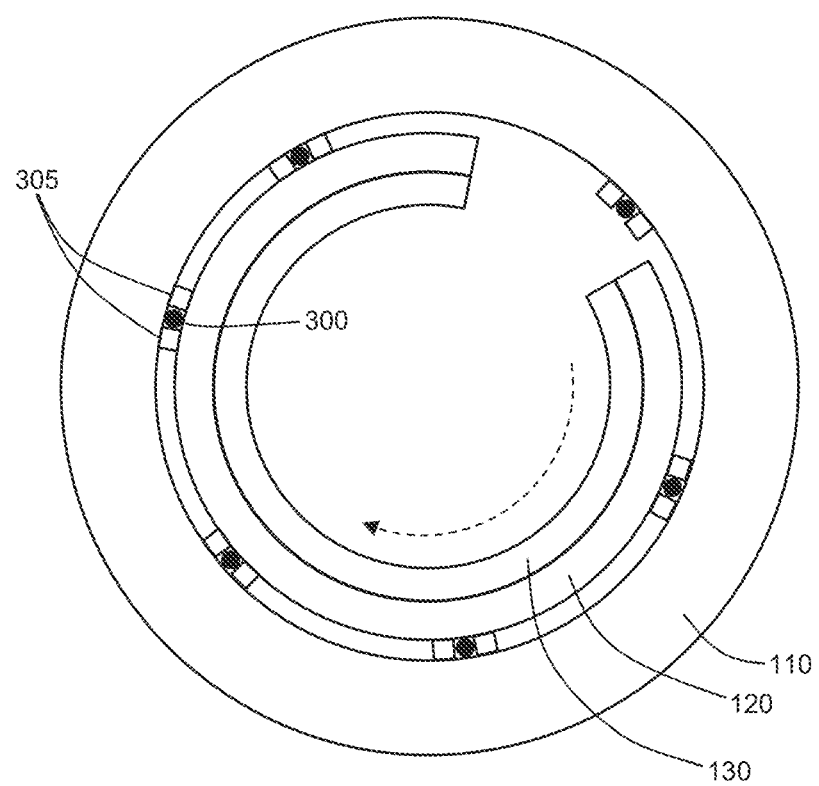
FIG. 5A is a diagram illustrating a mechanism for supporting or facilitating the rotation of the coil assembly within the magnet bore, in accordance with an embodiment of the present disclosure.

Referring to FIG. 5A, this diagram illustrates a mechanism for supporting or facilitating the rotation of the coil assembly, comprising gradient coil 120 and transmit coil 130, within the bore magnet 110, in accordance with an embodiment of the present disclosure. In some embodiments, support structures are provided to support the weight of the coil assembly in order to assist with, and/or guide, rotation of the coil assembly. In the example shown, a plurality of rotatable supports 300, such as rods, wheels, or bearings (which may be configured to be shock absorbing) are provided at various azimuthal positions. Such supports may be retained by a suitable mechanism, such as lateral retention mechanism 305. In some embodiments, such supports may be provided only in the vicinity of the lower portion of the system, where the weight of the coil assembly is received. Alternatively, pneumatic or air-bearing mechanisms may be employed.

Still referring to FIG. 5A, a wide variety of mechanisms and means, both manual and automated, may be employed to achieve or actuate rotation of the rotatable insert. In one example, an MRI-compatible motor is employed to produce rotation of the rotatable coil assembly. A floating cable may be employed that extends out the back of the magnet and is of sufficient length to support rotation.

Figure 5B:
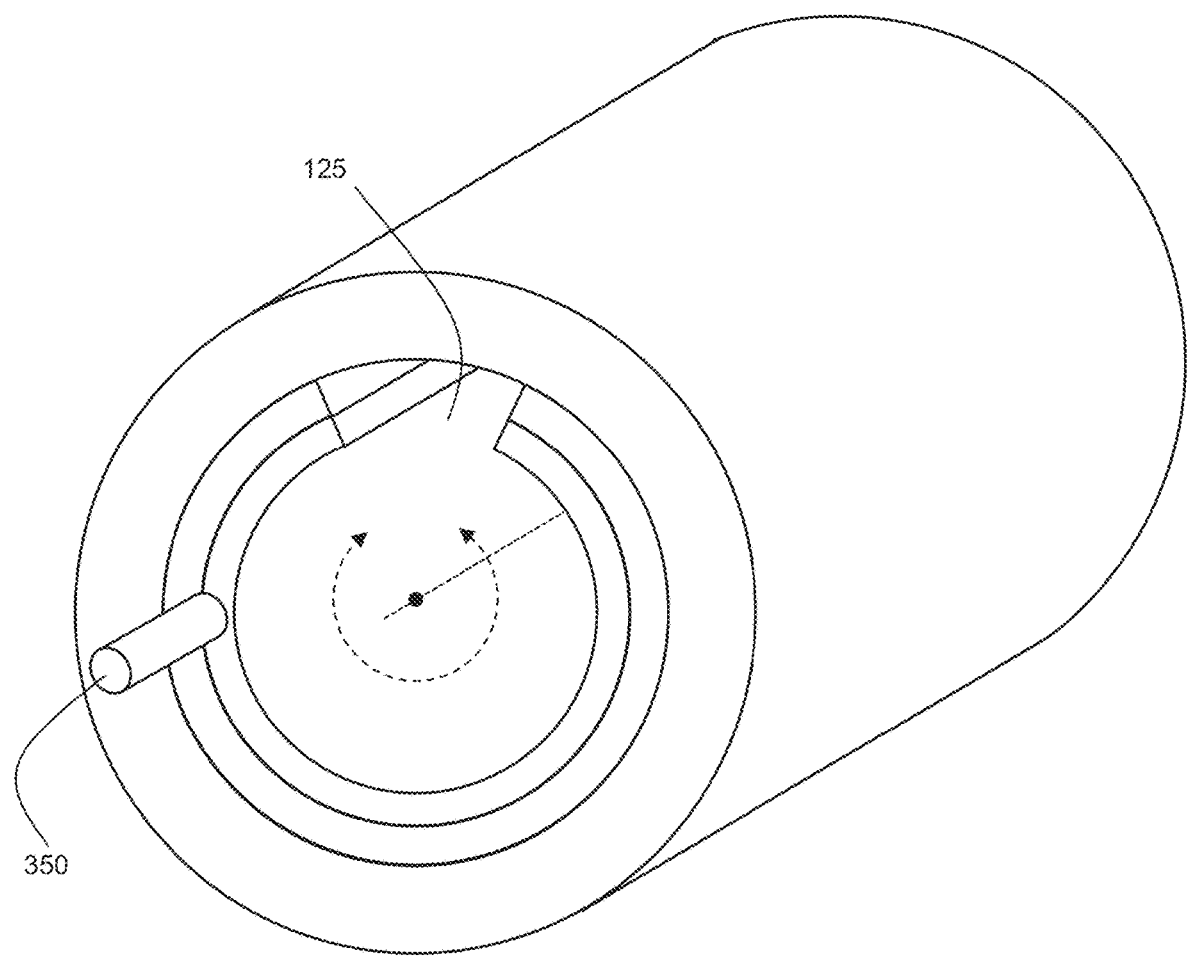
FIG. 5B is a diagram illustrating a handle coupled with the rotatable coil assembly, in order to provide manual or automated rotation actuation, in accordance with an embodiment of the present disclosure.

Referring to FIG. 5B, this diagram illustrates a handle 350 attached to the rotatable coil assembly, in order to provide manual or automated rotation actuation and relative positioning of aperture 125, in accordance with an embodiment of the present disclosure.

Figure 5C:
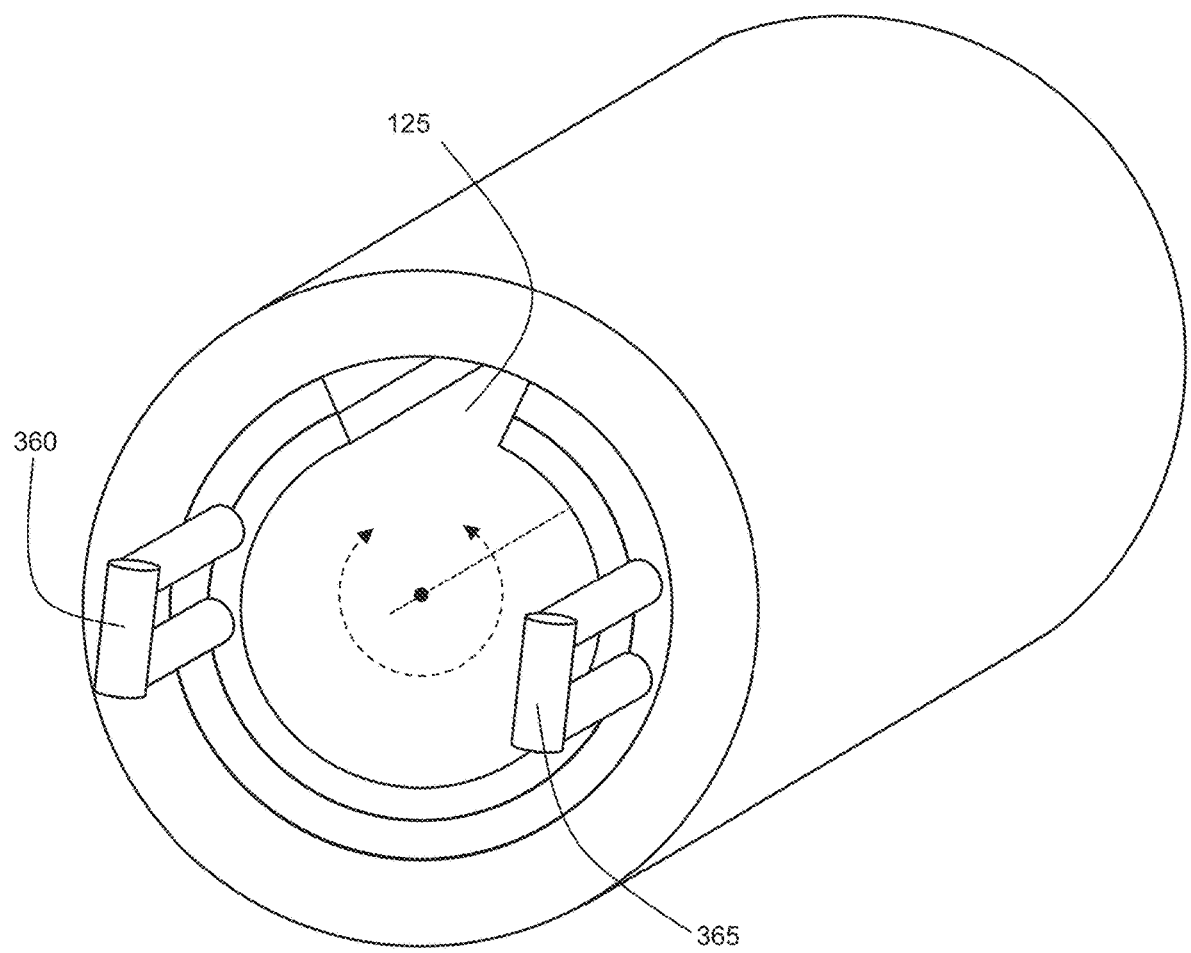
FIG. 5C is a diagram illustrating dual handles coupled with the rotatable coil assembly, in order to provide manual or automated rotation actuation, in accordance with an embodiment of the present disclosure.

Referring to FIG. 5C, this diagram illustrates dual handles 360 and 365 are attached to the rotatable coil assembly, in order to provide manual or automated rotation actuation and relative positioning of aperture 125, in accordance with an embodiment of the present disclosure. The dual handles 360 and 365 are coupled with an automated mechanism, such as an external motor, to automatically control the rotation of the coil assembly. In some embodiments, the dual handles 360 and 365 are provided at the rear of the system, such that they do not interfere with the body of the patient, e.g. the patient's shoulders.

Figure 5D:
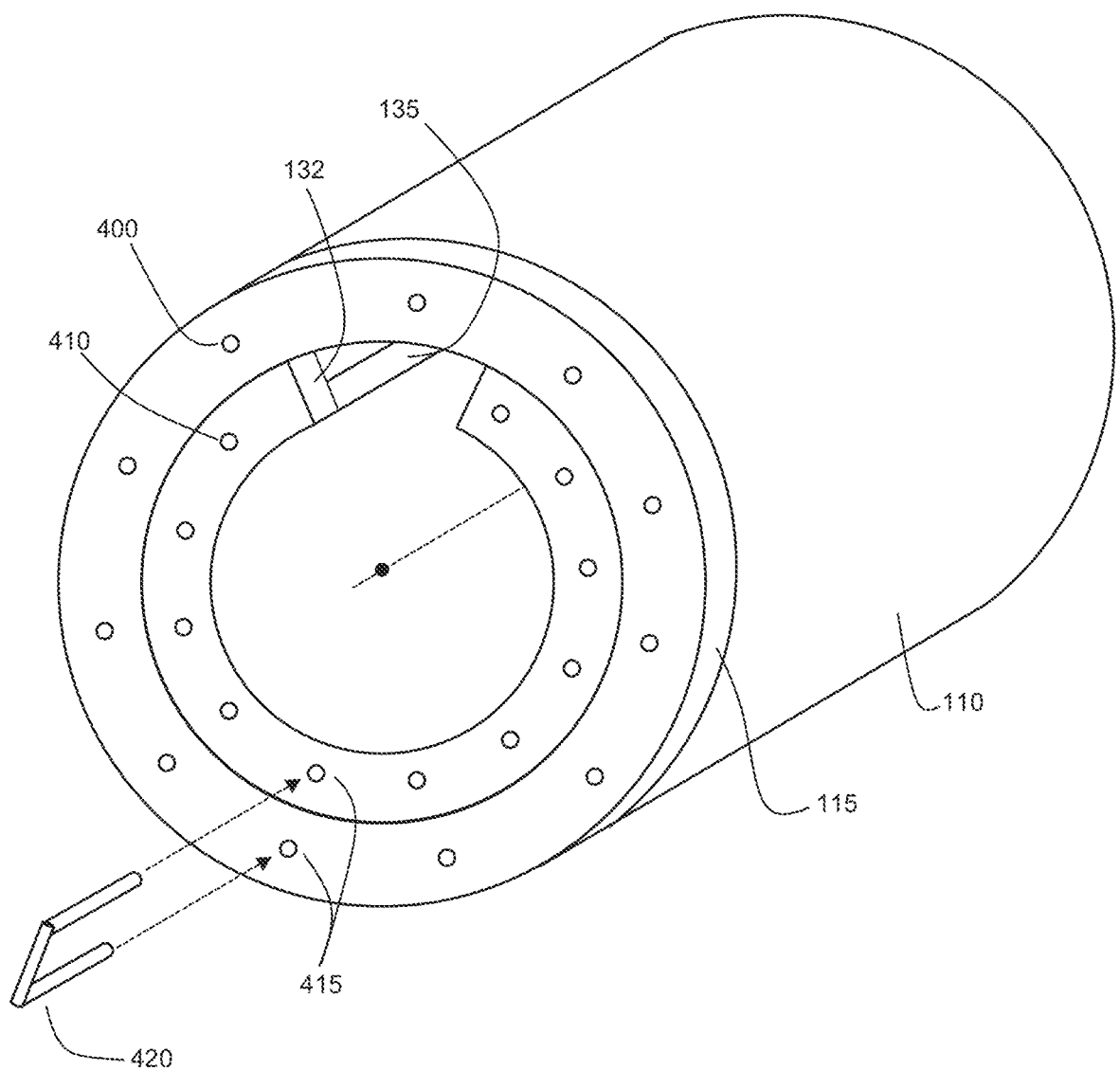
FIG. 5D is a diagram illustrating a locking mechanism that enables the angular orientation of the rotatable coil assembly to be locked at a plurality of configurations, in accordance with an embodiment of the present disclosure.

Referring to FIG. 5D, this diagram illustrates an implementation of a locking mechanism that enables the angular orientation of the rotatable coil assembly to be locked at a plurality of configurations, in accordance with an embodiment of the present disclosure. End portions 132 and 115 are provided on coil assembly 135 and solenoid 110, respectively. The end portion 132 comprises a plurality of first holes 410, and end portion 115 comprises a plurality of second holes 400. As coil assembly 135 is rotated, first holes 410 and second holes 400 align at different angular positions. A locking member 420 can be inserted to lock an angular position at a location where holes align, such as at location 415.

Figure 5E:
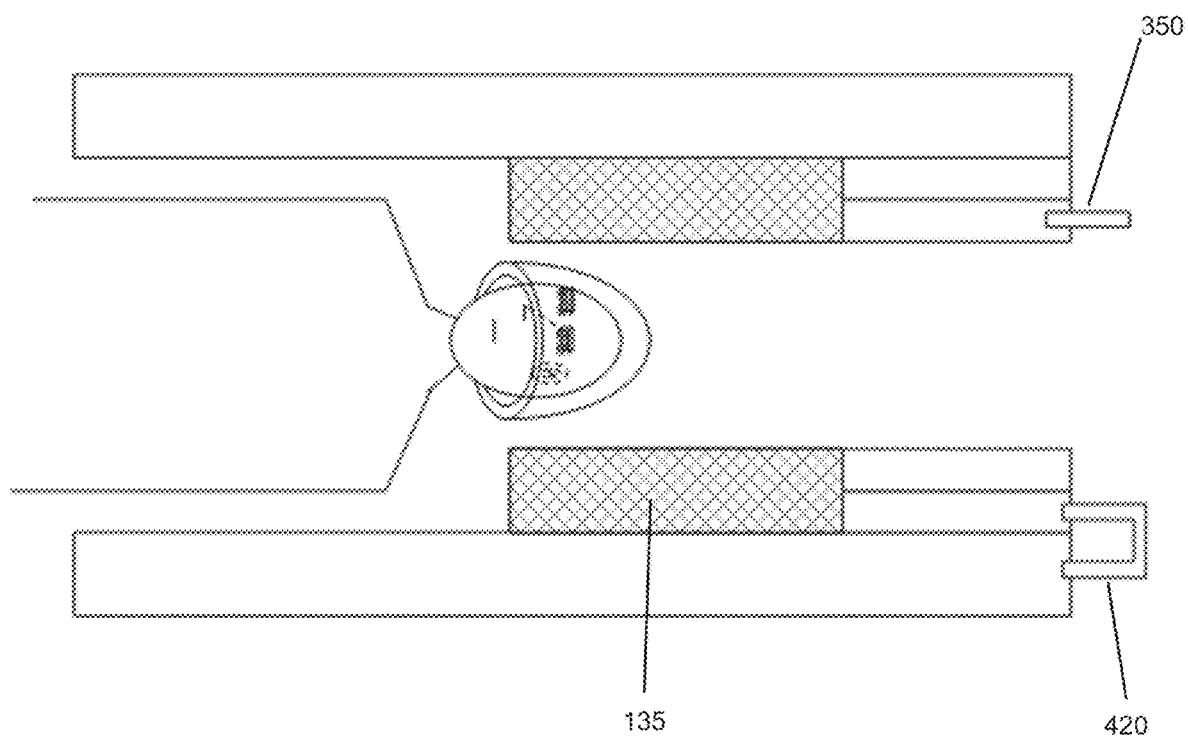
FIG. 5E is a diagram illustrating a magnetic resonance imaging system comprising a rotatable coil assembly, at least one rotation mechanism (such as the handle as shown), and an optional locking mechanism, such as the insertable locking member as shown, in accordance with an embodiment of the present disclosure.

Referring to FIG. 5E, this diagram illustrates an implementation of a magnetic resonance imaging system comprising a rotatable coil assembly 135, at least one rotation mechanism, such as handle 350, and an optional locking mechanism, such as the insertable locking member 420, in accordance with an embodiment of the present disclosure.

Figure 5F:
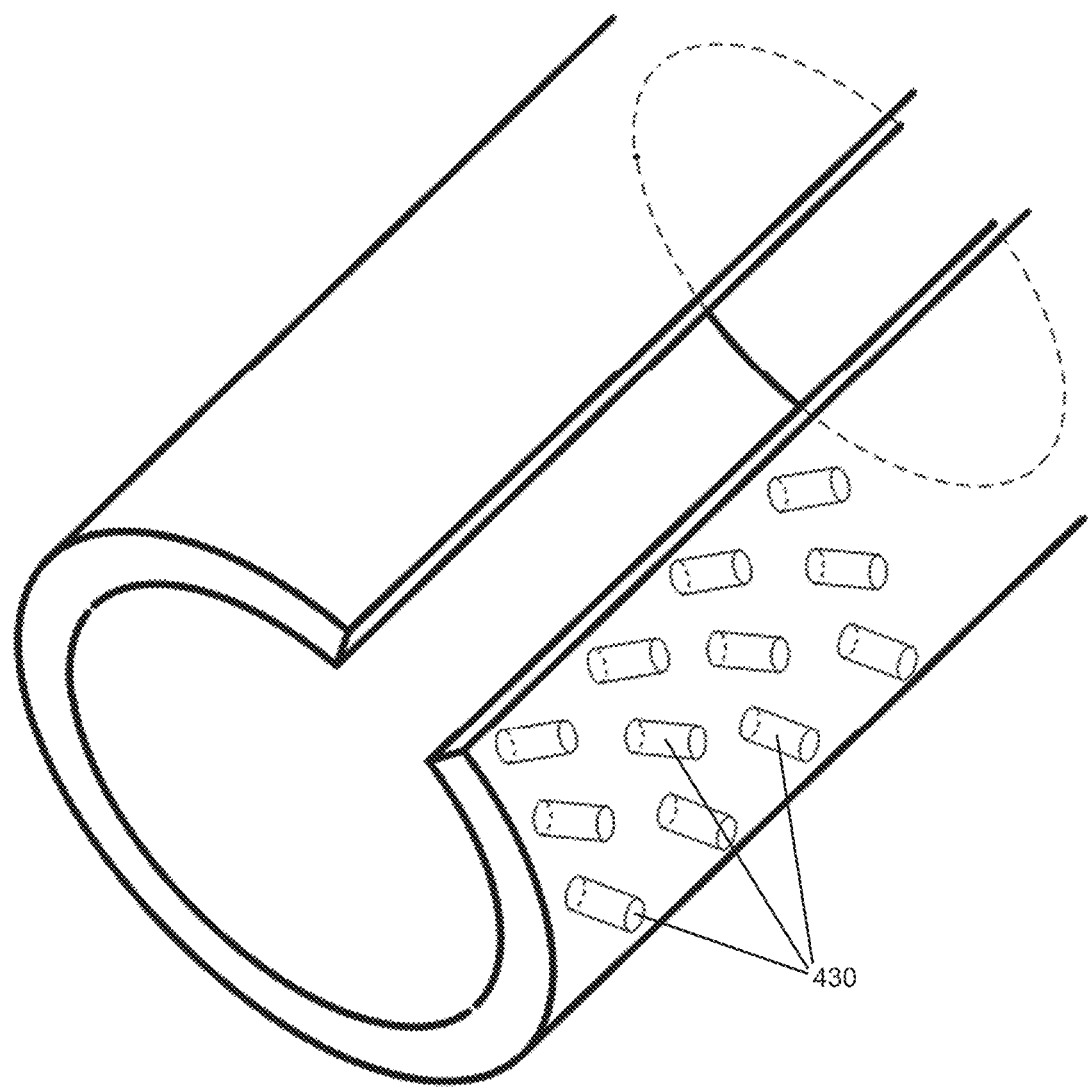
FIG. 5F is a diagram illustrating a locking mechanism in which a plurality of spring-loaded rods are disposed at the outer surface of coil assembly, the locking mechanism removably receivable in corresponding holes within a solenoid for locking a given angular orientation, in accordance with an embodiment of the present disclosure.

Referring to FIG. 5F, this diagram illustrates a plurality of spring-loaded rods 430 may be provided at the outer surface of coil assembly, which may be removably received in corresponding holes within the solenoid for locking a given angular orientation, in accordance with an embodiment of the present disclosure. The rods may be disengaged by a suitable mechanism. In another embodiment, the rods may be received at a sufficiently shallow depth that they may be disengaged by applying a sufficient torque to the coil assembly.

Figure 6A:
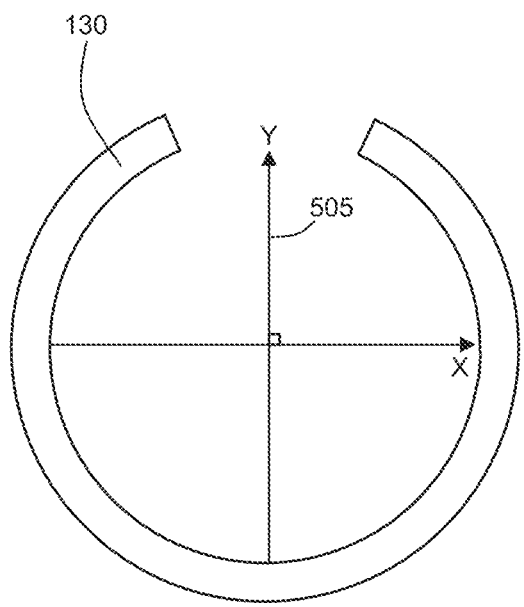
FIGS. 6A and 6B, together, are diagrams illustrating configurations of the gradient coil, in accordance with some embodiments of the present disclosure
Figure 6B:
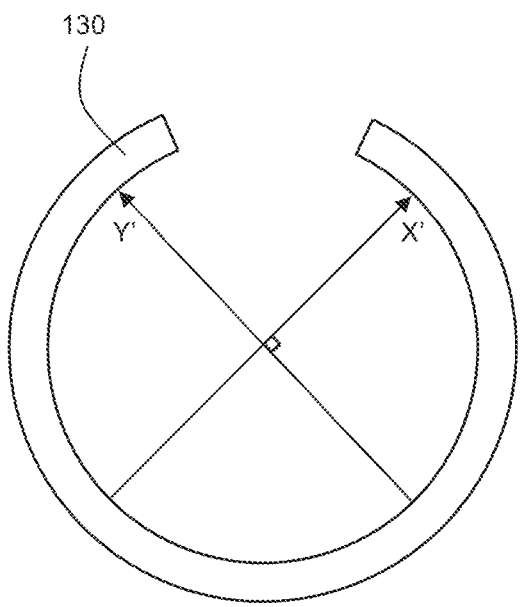

Referring to FIGS. 6A and 6B, together, these diagrams illustrate configurations of the gradient coil 130, in accordance with some embodiments of the present disclosure. FIG. 6A illustrates the Y gradient axis 505 being directed toward the aperture on the coil assembly 350, and the presence of the aperture leads to a performance degradation of the Y-gradient relative to that of the X-gradient. FIG. 6B illustrates another configuration in which the X and Y orientations are rotated relative to those shown in FIG. 14(a), thereby improving the relative performance of the Y gradient. In one example implementation, the X and Y axes are rotated such that they are angled at approximately 45 degrees relative to the normal defined by the aperture and neither X nor Y axis is directed towards the aperture of coil assembly 130.

Figure 6C:
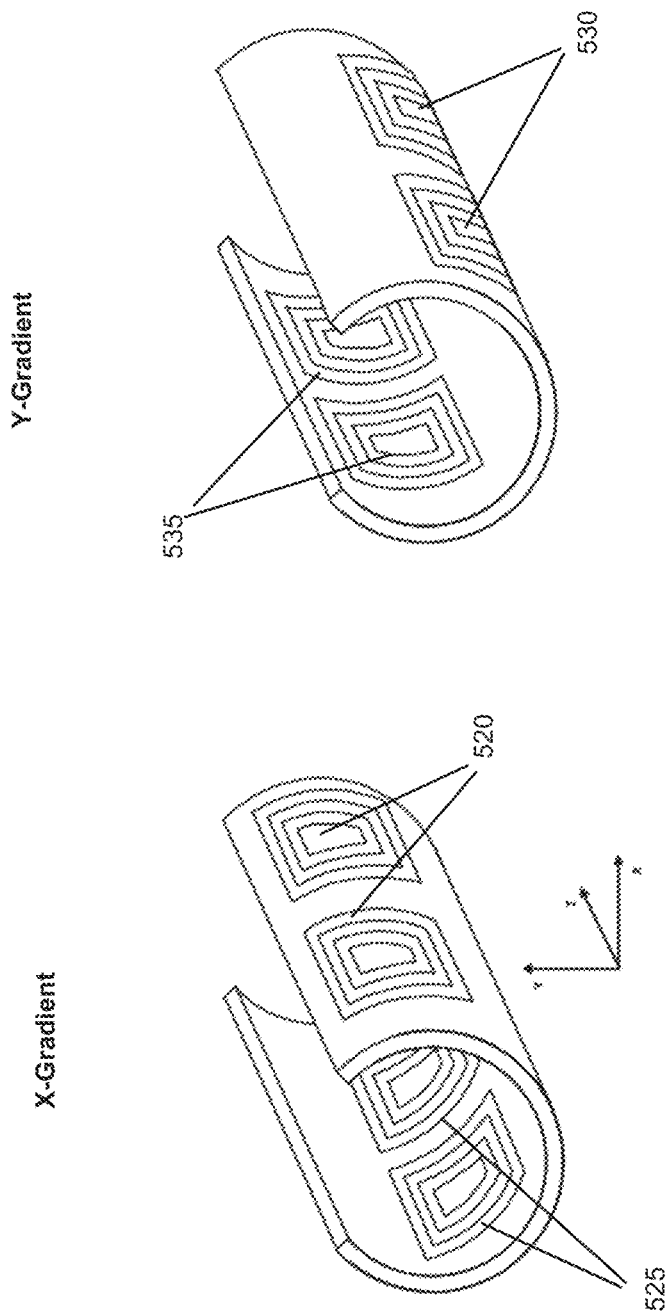
FIG. 6C is a diagram illustrating gradient coils, the example X and Y coil configurations, as shown in FIG. 6B, in accordance with an embodiment of the present disclosure.

Referring to FIG. 6C, this diagram illustrates an implementation of gradient coils, as shown in FIG. 6B, e.g., the example X (520 and 525) and Y (530 and 535) coil configurations, in accordance with an embodiments of the present disclosure. The reoriented coil configurations improve the Y gradient at the expense of the X gradient. The Y gradient improves in performance because there is available continuous surface area for current to flow on either side of the newly defined Y axis (Y') in FIG. 6B, while in FIG. 6A there is only continuous surface area for current flow on one side of the Y axis (the lower half). Likewise, the X gradient will suffer slightly in performance, for at least that, as shown in FIG. 6A, ample surface area exists for current to flow on either side of the X axis, while, as shown in FIG. 6B, the surface area on one side of the X' axis has been diminished. A variation on this approach allows for the 'z' axis to remain a complete cylinder (to achieve full performance) while the 'x' and 'y' axes are rotated about the aperture. In this approach, a substantial aperture is formed without sacrificing gradient performance.

Referring back to FIGS. 1A-6C, the various embodiments, described above, may provide one or more of the following advantages. For example, various embodiments may provide for a smaller head-only MRI system that fits closely around a patient's head, and meets the requirement to fit anesthesia equipment, other MRI imaging coils such as a port coil, or to accommodate the variety of patient positions possible during, for example, neurosurgery (or spine surgery). Such embodiments may lower costs (relative to larger size MRI systems), reduce difficulty in siting, and reduce difficulty in moving the device, all of which are linked to the size of an MRI.

Still referring back to FIGS. 1A-6C, more generally, embodiments may make an MRI a less uncomfortable experience. Embodiments may make the patient feel less isolated within the scanner with a greater ability to communicate with the outside world. Once the scan starts, the patient can be provided with knowledge of how much time remains in some embodiments. The reduced feeling of isolation, greater ability to communicate, and/or knowledge of how much time remains can decrease fidgeting, which may prevent some degradation of image quality. This may be particularly advantageous with respect to children, as they have a tendency to move about once isolated in the scanner. Similarly, this may be advantageous for patients in medical distress, as it is difficult to have them be isolated and away from medical attention for the duration of their time in the scanner.

Still referring back to FIGS. 1A-6C, furthermore, during an interventional neurosurgical procedure, it is advantageous for the anesthetist to have visual access to the patient's face. For an intra-operative procedure to maintain this visual access, prone and other patient positions can be challenging, but embodiments described above can reduce or eliminate these challenges.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed:

1. A method of imaging by way of a portable magnetic imaging (MRI) system, comprising:
   placing a portion of the subject in relation to at least one coil assembly disposed in relation to a magnet that is configured to generate a magnetic field, placing comprising providing the magnet, and providing the magnet comprising providing a portable magnet transportable on a cart; and
   initiating an imaging sequence to image the subject using the at least one coil assembly and the magnet.

2. The method of claim 1, further comprising:
   rotating the at least one coil assembly relative to the magnet such that a portion of the subject is aligned with an apparatus, wherein at least a portion of the apparatus is housed in relation to the at least one coil assembly; and
   fixing the at least one coil assembly relative to the magnet before initiating the imaging sequence
   wherein the at least one coil assembly comprises at least one annular coil assembly,
   wherein the at least one coil assembly has an aperture formed therein that extends longitudinally along a central axis of the magnet to an edge of the magnet, and
   wherein the at least one coil assembly and the magnet are rotatable relative to each other.

3. The method of claim 2, further comprising at least one of:
   loading the subject on a slidable table;
   sliding the table into an inner bore of the magnet;
   inserting at least one radio-frequency (RF) receiver coil into the aperture of the at least one annular coil assembly before initiating the imaging sequence.

4. A method of providing a portable magnetic resonance imaging (MRI) system, comprising:
   providing a magnet configured to generate a magnetic field, providing the magnet comprising providing a portable magnet transportable on a cart; and
   providing at least one coil assembly disposed in relation to the magnet, providing the at least one coil assembly comprising providing at least one gradient coil, providing the at least one coil assembly and the magnet comprising providing the annular coil assembly and the magnet as rotatable relative to each other.

5. The method of claim 4, further comprising providing a rotating mechanism configured to rotate the at least one coil assembly relative to the magnet,
   wherein providing at least one coil assembly comprises providing at least one annular coil assembly,
   wherein providing the at least one coil assembly comprises forming an aperture therein that extends longitudinally along a central axis of the magnet to an edge of the magnet, and
   wherein providing the at least one coil assembly comprises providing the at least one coil assembly as rotatable and relative to the magnet.

6. The method of claim 5, further comprising providing at least one of: a patient table slidable within the at least one annular coil assembly; a display device; a projection screen; and a camera disposed within the aperture.

7. The method of claim 4, further comprising providing at least one radio-frequency (RF) coil sized to accommodate a subject's head.

8. The method of claim 5, wherein one of:
   forming the aperture comprises forming the aperture with a length in a range that is shorter than a longitudinal length of the at least one annular coil assembly, and
   forming the aperture comprises forming the aperture with a length in a range of approximately that of the longitudinal length of the at least one annular coil assembly.

9. The method of claim 5, wherein one of:
   forming the aperture comprises forming the aperture with at least one of: at least one gradient axis; and at least one shield,
   forming the aperture comprises forming the aperture as extending along a longitudinal direction of the at least one annular coil assembly,
   forming the aperture comprises disposing the aperture in the upper hemisphere of the at least one annular coil assembly,
   forming the aperture comprises disposing the aperture in the lower hemisphere of the at least one annular coil assembly,
   providing the at least one annular coil assembly further comprises providing at least one transmit coil,
   forming the aperture comprises sizing the aperture to accommodate at least one of: at least a portion of a breathing apparatus, an intra-operative device, an infusion apparatus, a display device, a projection screen, and a camera, providing the at least one gradient coil comprising configuring each at least one gradient coil to provide a gradient variation to the static magnetic field in a plurality of spatial directions, and forming the aperture comprises disposing the aperture, wherein none of the plurality of spatial directions are directed at the aperture of the at least one annular coil assembly.

10. The method of claim 7, wherein providing the at least one RF coil comprises configuring the at least one RF coil to receive radio-frequency signals emitted from within the subject's head.

11. The method of claim 10, wherein providing the coil assembly comprises sizing the coil assembly to accommodate the at least one RF coil.

* * * * *